United States Patent
Kessler et al.

(10) Patent No.: US 8,282,831 B2
(45) Date of Patent: Oct. 9, 2012

(54) METHOD AND APPARATUS FOR CHROMATOGRAPHIC COMPONENT, SEPARATION WITH PARTIAL RECIRCULATION OF MIXTURE FRACTIONS

(75) Inventors: Lars Kessler, Magdeburg (DE); Andreas Seidel-Morgenstern, Magdeburg (DE)

(73) Assignee: Max-Planck-Gesellschaft zur Foderung der Wissenchaften e. V. (DE)

( * ) Notice: Subject to any disclaimer, the term of this patent is extended or adjusted under 35 U.S.C. 154(b) by 425 days.

(21) Appl. No.: 12/596,392

(22) PCT Filed: Apr. 16, 2008

(86) PCT No.: PCT/EP2008/054571
§ 371 (c)(1),
(2), (4) Date: Oct. 16, 2009

(87) PCT Pub. No.: WO2008/125679
PCT Pub. Date: Oct. 23, 2008

(65) Prior Publication Data
US 2010/0186587 A1  Jul. 29, 2010

(30) Foreign Application Priority Data
Apr. 17, 2007 (EP) .................................. 07007765

(51) Int. Cl.
*B01D 15/08* (2006.01)
*B01D 15/18* (2006.01)
(52) U.S. Cl. ...................... 210/659; 210/198.2; 210/656
(58) Field of Classification Search ............... 210/198.2, 210/656, 659
See application file for complete search history.

(56) References Cited

U.S. PATENT DOCUMENTS

| | | | |
|---|---|---|---|
| 2,985,589 A | 5/1961 | Broughton et al. | |
| 4,478,721 A * | 10/1984 | Gerhold | 210/659 |
| 5,102,553 A | 4/1992 | Kearney et al. | |
| 5,470,464 A * | 11/1995 | Priegnitz | 210/198.2 |
| 5,719,302 A * | 2/1998 | Perrut et al. | 554/191 |
| 6,136,198 A * | 10/2000 | Adam et al. | 210/659 |
| 6,685,781 B2 * | 2/2004 | Hyoky et al. | 127/46.1 |

(Continued)

FOREIGN PATENT DOCUMENTS

WO     0025885     5/2000

(Continued)

OTHER PUBLICATIONS

English translation of the International Preliminary Report on Patentability for PCT/EP2008/054571 issued Nov. 10, 2009.*

(Continued)

*Primary Examiner* — Robert Clemente
(74) *Attorney, Agent, or Firm* — Lowe Graham Jones PLLC

(57) ABSTRACT

A method for the chromatographic separation of components of a multicomponent fluid mix by means of the simulated moving bed method wherein the multicomponent fluid mix and at least one solvent are fed to inflows of a plurality of chambers containing at least one solid substance and connected to each other in series to form a closed loop. An extract stream containing at least one first component separated from the multicomponent fluid mix as well as a raffinate stream containing at least one second component separated from the multicomponent fluid mix are carried out of the chambers through a first and second outflows. At least part of the raffinate stream and/or extract stream carried off at the first and/or second outflows is preliminarily stored and recirculated to the first and/or second inflow of the chambers alternately or simultaneously with the multicomponent fluid mix and/or the solvent within one clock unit.

20 Claims, 5 Drawing Sheets

U.S. PATENT DOCUMENTS

| | | | |
|---|---|---|---|
| 6,752,929 B1 * | 6/2004 | Zahr et al. | 210/659 |
| 6,843,854 B2 * | 1/2005 | Farrenburg et al. | 127/24 |
| 7,479,228 B2 * | 1/2009 | Schramm et al. | 210/659 |
| 7,615,159 B2 * | 11/2009 | Strube et al. | 210/659 |
| 8,008,536 B2 * | 8/2011 | Winter et al. | 585/820 |
| 2003/0229213 A1 | 12/2003 | Farrenburg et al. | |
| 2005/0230297 A1 * | 10/2005 | Ogawa | 210/198.2 |

FOREIGN PATENT DOCUMENTS

| | | |
|---|---|---|
| WO | 2004014511 | 2/2004 |
| WO | 2005113101 | 12/2005 |
| WO | WO 2005113101 A2 * | 12/2005 |
| WO | 2006023459 | 3/2006 |

OTHER PUBLICATIONS

Bae et al., "Partial-Discard Strategy for Obtaining High Priority Products Using Simulated Moving Bed Chromatography," Science Direct, Journal of Chromatography, A, 1122, pp. 161-173. 2006.

* cited by examiner

METHOD AND APPARATUS FOR CHROMATOGRAPHIC COMPONENT, SEPARATION WITH PARTIAL RECIRCULATION OF MIXTURE FRACTIONS

PRIORITY CLAIM

This is a national phase application of PCT/EP2008/054571 filed Apr. 16, 2008 which claims priority to European Application Serial No. 07007765.6 filed Apr. 17, 2007, contents of which are incorporated herein.

FIELD OF THE INVENTION

The invention relates to a method and apparatus for the chromatographic separation of components of a multicomponent fluid mix.

BACKGROUND

Methods for the chromatographic separation of components of a multicomponent fluid mix according to the current state of the art are used in particular in the pharmaceutical and chemical industries for separating components of a mixture of substances having a high degree of purity even if this mixture of substances is a complex multicomponent fluid mix, the components of which might additionally be temperature-sensitive. Here, the different affinities of the components to be separated compared to a solid substance (preferably adsorbent material) are used for the separation thereof.

Conventionally, chromatographic separations are carried out discontinuously in a so-called batch process. In such a batch process, a solvent (eluant) is passed through a chamber (separation column) filled with the solid material. A limited amount of the sample to be separated is injected into a solvent stream. Due to the differences in the strength of the interactions, the components move through the separation column at different velocities and exit these at different times. This injection cannot be repeated until after a certain period of time, without affecting the separation success of the previous injection.

For a continuous operating mode, a counterflow between the liquid phase containing solvent and the solid phase is generated. To this end, the solid phase is moved in the opposite direction to the liquid phase.

In such an operating mode in a counterflow process, the multicomponent fluid mix may be applied continuously at the centre of the separation column. In the case of suitably selected flow ratios between the liquid and the solid phases, the component moving together with the solid substance and showing the stronger interaction may be fed in the direction of an extract stream carried out of the separation column and the component moving together with the liquid phase and showing the weaker interaction may flow in the direction of a raffinate stream also carried out.

The separation methods may be carried out in a continuous operating mode according to the known Simulated Moving Bed (SMB) method. Such methods are applied to apparatus which as a rule consist of at least four separation zones forming a loop, which consist of at least one chamber or chamber section. The actual counterflow of the solid phase is simulated by periodically moving the solid substance statically placed in individual chambers in the direction opposite to the flow of the solvent. This corresponds to the Moving Column principle. Alternatively, in the case of fixed chambers, also the positions of the inflow and outflow ports may be cyclically displaced. This corresponds to the Moving Port principle. The time between two switch-over processes is identified as the clock time. The zones are delimited by two inflows, one each for the multicomponent fluid mix and for the solvent, as well as by two outflows, one each for the extract and the raffinate stream. The separation of the components is for the most part carried out in two of the four zones, whereas the two further zones are used for the regeneration of the solid and liquid phases.

In such an SMB method, a self-repeating regime will develop after a certain period of time. This will be referred to as a cyclic steady state. In this state, characteristic concentration profiles, which repeat themselves after one clock period and which are caused by the periodic changeover, are present in the outlet streams.

U.S. Pat. No. 2,985,589 describes such an SMB method for the continuous chromatographic separation of multicomponent fluid mixes having a fixed adsorbent bed containing the solid substance as well repositionable inflows and outflows.

The method described in U.S. Pat. No. 2,985,589 is carried out at constant operation parameters such as the volume streams fed in and out, the time duration of a clock unit and the concentrations of the multicomponent fluid mix and the solvent fed in. It will be referred to below as the "conventional method".

U.S. Pat. No. 5,102,553 describes an SMB method wherein the volume streams of the multicomponent fluid mix, the solvent, the extract stream, the raffinate stream and the in-circuit circulation streams, which are fed in and out, are designed to be time-variable within one clock unit (the "powerfeed" method). By this means, productivity may be enhanced compared to the SMB method at constant operation parameters.

In WO A 0025885 a process is suggested which provides for an asynchronous switching over of inflows and outflows. This corresponds to the VariCol method. Contrary to the conventional SMB method, the port positions of the inflows and outflows are newly positioned here at different points in time, so that variable separation zone lengths per unit time are obtained. In this way, an increase of productivity is achieved.

US 2006/023459 shows a variation of the VariCol method, wherein the concentration of the stream between two zones is increased by means of an additional process step.

WO 2004014511 describes an SMB method wherein the concentration of the multicomponent fluid mix fed in is changed within one clock unit. This corresponds to the Modi-Con method.

By means of this method, an increase of productivity and of the product concentration as well as a reduction of the specific solvent use may be achieved by feeding in a higher concentrated multicomponent fluid mix for example in the fourth quarter of a clock period.

U.S. Pat. No. 2,985,589, U.S. Pat. No. 5,102,553 and WO 2004014511 describe methods which are based on a continuous collection of the effluent extract and raffinate streams. These methods have to be implemented in such a way that a specified high integral purity averaged across the entire clock period may be achieved. In the case of very high target purities, this is achieved at the cost of a lower productivity.

As an alternative, an SMB method is suggested in Y.-S. Bae and C.-H Lee "Partial discard strategy for obtaining high purity products using movid bed chromatography", Journal of Chromatography A, 1122: 161-173 (2006), wherein only part of the effluent extract or raffinate stream is collected within one clock period (fractionation method). In the method described, the part not collected is discarded. A recirculation of the non-collected proportion into the receiver tank of the initial multicomponent fluid mix is suggested only for the case in which this tank is large and the proportion to be recirculated is small, in order to make sure that the inflow concentration of the multicomponent mix will not be changed. The method described in the Journal of Chromatography A, 1122: 161-173 (2206) has the disadvantage that a partial discarding of the outflow stream will cause reductions in productivity and yield.

SUMMARY

Consequently, the present invention is directed to providing a method for the chromatographic separation of components of a multicomponent fluid mix by means of the Simulated Moving Bed method, which enables a high productivity at a high specified degree of purity of the components to be separated as well as a reduction of the operating costs to be achieved. An apparatus for carrying out the method is provided.

In a preferred embodiment according to the invention, in a method for the chromatographic separation of components of a multicomponent fluid mix by means of a Simulated Moving Bed process, at least part of the raffinate stream and/or extract stream carried off through the first and/or second outflows is preliminarily stored in at least one container, respectively, and is fed to the first and/or the second inflow alternately or simultaneously with the multicomponent fluid mix and/or the solvent in a recirculation mode to the chamber or chamber sections within one clock unit. To this end, the multicomponent fluid mix and at least one solvent are fed to a plurality of chambers or chamber sections containing at least one substance at the first and second inflows, and the extract stream containing at least one first component separated from the multicomponent fluid mix as well as the raffinate stream which contains at least one second component separated from the multicomponent fluid mix, are carried out of the chambers or chamber sections through first and second outflows. The chambers or chamber sections form a closed loop and are thus connected to each other in series. The connection ports of the first and second inflows and outflows, which are respectively positioned between two chambers or chamber sections of the loop, are newly positioned at the end of a cyclic clock unit between two further chambers or chamber sections of the loop.

In such a method, at least one of the two effluent streams is partially collected within one clock unit, which results in at least two partial flows per outflow, of which at least one is collected in at least one tank and the content of which is introduced into the separation apparatus within a defined period of time within the clock period in a freely selectable infeed regime alternately or simultaneously with the initial multicomponent fluid mix. Thus, the recirculated stream will not be mixed with the original multicomponent fluid mix. Rather, the differences in the concentrations of the components and their ratios amongst each another are, according to the invention, intentionally used in order to achieve an increase of purity. In contrast to the ModiCon method, if the initial multicomponent fluid mix is not fed into the system, an already pre-separated fraction is introduced, in which the ratio of components is shifted in favour of at least one component. The ModiCon method is based on the utilisation of non-linearities of the adsorption isotherms, which as a limitation is not the case with the subject matter of the present invention.

Thus, the stream branched off is collected in one or several containers, for example in the form of tanks, and is subsequently introduced into the apparatus within a defined period of time, which is cyclically repeated, within that clock period in a defined infeed regime preferably alternately with the actual multicomponent fluid mixes introduced. The partial stream not recirculated which reaches the specified degree of purity, is carried out of the system and is collected in a storage medium provided for this purpose. This approach allows an increase in the productivity of the process to be achieved with the given purities.

Thus, according to the invention the multicomponent fluid mix, the content of at least one of the containers (recycle tank) which is provided for the storage of the proportion of the raffinate and/or extract stream to be recirculated and which thus contains at least one of the components, and at least one solvent of a plurality of chambers or chamber sections containing at least one solid substance, preferably adsorbent material, is fed to a first or a second inflow. At a defined point in time within the clock period, the inflow either from a container which contains exclusively the multicomponent fluid mix is switched over to at least one recycle tank or the inflow from at least one recycle tank is switched over to the container of the multicomponent fluid mix. This is carried out by means of a valve. The point in time and the order of such a switch-over have an effect on the separation performance of the apparatus for implementing the method according to the invention.

Within the clock period, at least one of the components or outflow streams carried out of the apparatus is diverted into at least one of the recycle tanks.

At the end of the cyclically repeating clock period, the chambers will be shifted by means of a multi-position valve by one position in the direction opposite to the flow of the fluidic mass. Alternatively, the connection ports of the first and second inflows and outflows, which are respectively positioned between two chambers and chamber sections of the loop, are newly positioned at the end of the cyclic clock period between two further chambers or chamber sections of the loop.

An operation in an open loop ("Open Loop SMB") is also possible. In this case, the regeneration zone of the liquid phase may be omitted. The number of zones is reduced to three.

Advantageously, the subject matter of the present invention may be applied to conventional SMB methods and the apparatus implementing them. Also a combination of the method according to the invention with methods varying the volume stream of the inflowing multicomponent fluid mix within one clock period ("Powerfeed") is possible. In the case of any non-linear adsorption isotherms being present, a combination with the ModiCon method is also possible. Moreover, the method according to the invention may be used for processes using asynchronous switching times ("VARICOL").

The recirculation-based infeed of the raffinate stream carried off and/or the extract stream carried off may be carried out within a clock unit following the carrying off or may be carried out within the same clock unit.

According to a preferred embodiment, in at least one first time section of the clock unit, the entire raffinate stream and/or extract stream carried off may be lead away as a product having the desired degree of purity, and in at least one second time section of the clock unit, the entire raffinate stream and/or extract stream carried off may be fed in on a recirculation basis.

Both the pressure and the temperature of the infed multicomponent fluid mix and/or of the solvent may be modified within one clock unit in a stepwise and/or continuous mode.

The composition of the solvent as well as the content of at least one modifier additionally introduced in the multicomponent fluid mix may preferably be modified in a stepwise and/or continuous mode.

According to a preferred embodiment, at least one solid substance is used which is suitable for producing different velocities of movement of the individual components of the multicomponent fluid mix in the individual chambers or chamber sections. This may be an adsorbent material.

According to a preferred embodiment, a mixture of a plurality of fluids and/or a mixture of at least one fluid with a low or high molecular modifier may be used as the solvent.

A gas or a mixture of a plurality of gases, which is/are in the supercritical or the sub-critical state, may be used as the solvent and/or the multicomponent fluid mix.

The solvent may also contain components to be separated. Here, the solvent with the components to be separated and the solvent without the components to be separated have various compositions and/or capacities with regard to influencing a binding behaviour of the components to be separated compared to the solid substance.

In the chambers or chamber sections, a chemical reaction for generating and separating components may be carried out.

The connection ports of the first and second inflows and outflows are newly positioned at different points in time.

At least one volume stream of the multicomponent fluid mix of the solvent, the extract stream, the raffinate stream and the in-circuit recirculation streams is modified in a stepwise and/or continuous mode within one clock unit.

The invention is also directed to an apparatus for the chromatographic separation of components of a multicomponent fluid mix the preferably comprises at least four chambers with interposed inflows or outflows. For branching off the proportion of the raffinate or extract stream which is carried off, a first valve which switches between the stream to be carried out of the apparatus and the stream to be recirculated, and a second valve which switches between the multicomponent fluid mix to be fed in and the stream to be recirculated into the apparatus are additionally provided. Between the first and the second valves, at least one container for preliminarily storing the branched-off stream is positioned.

Further advantageous embodiments will become evident from the dependent claims.

BRIEF DESCRIPTION OF THE DRAWING

Advantages and expediencies are to be taken from the description following below in conjunction with the drawings, wherein.

DETAILED DESCRIPTION OF THE INVENTION

Figure 1:
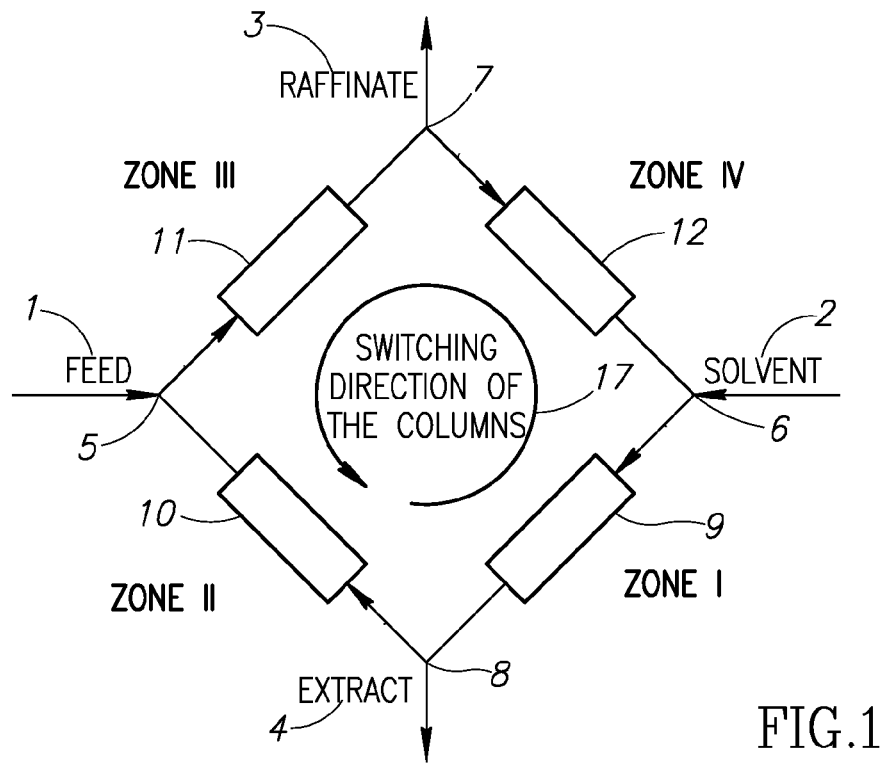
FIG. 1 shows a schematic view of an apparatus for carrying out a method for the chromatographic separation of components according to the SMB method known from the prior art, which operates according to the Moving Column principle.

FIG. 1 shows a schematic view of an apparatus for carrying out a method for the chromatographic separation according to the SMB method known from the prior art. A multicomponent fluid mix (feed) 1 together with a solvent (eluant) 2 is fed in at the inflow 5 and 6, respectively.

A raffinate stream 3 and an extract stream 4 are taken off at the outflows 7 and 8, respectively, of the apparatus. The apparatus consists of a total of four chambers 9, 10, 11 and 12 functioning as separation zones labelled zones I-IV respectively, which are connected to each other in series along pathways 13, 14, 15 and 16 indicating the flow pattern within the chambers to form a loop. Between the chambers 9, 10, 11 and 12, the connection ports for the inflows 5, 6 and the connection ports for the outflows 7, 8 are located.

A solid substance is present in a fixed manner in at least one of the four chambers 9-12, and the solvent flows through the chambers at different velocities. In order to generate the counterflow of the solid phase, the chambers are shifted periodically in a direction opposite to the flow of the liquid phase at the end of a clock unit or within a clock unit. The multicomponent fluid mix to be separated is fed centrally into the apparatus here in a continuous mode.

The positions of the inflows and outflows establish four zones, in which a different relative velocity of the liquid and solid phases is present as a result of a respectively different volume flow of the liquid phase. As a result of a suitable adjustment of these relative velocities, stronger adsorbing components will move together with the solid phase in the direction of an extract stream carried off and weaker adsorbing components will move together with the solvent in the direction of a raffinate stream carried off.

The separation of the components is predominantly carried out in zones II and III, whereas the zones I and IV are used for the regeneration of the solid substance, which may for example be an adsorbent material, and of the solvent.

The arrow 17 indicates the direction of the column switching, i.e. the Moving Column principle.

Figure 2:
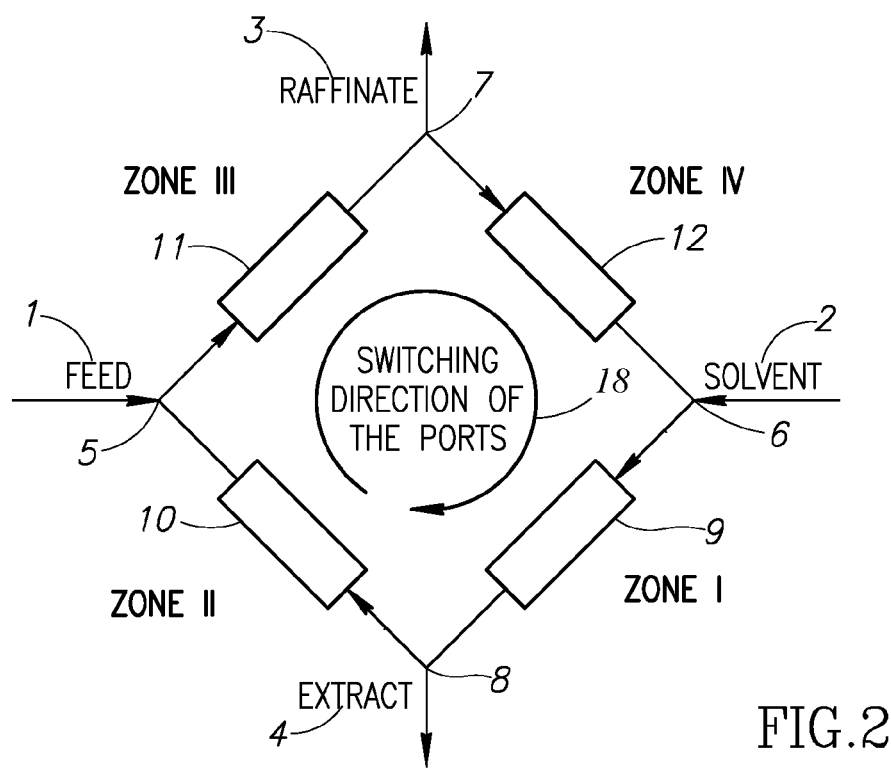
FIG. 2 shows a schematic view of an apparatus for carrying out a method for the chromatographic separation of components according to the SMB method known from the prior art, which operates according to the Moving Port principle.

The apparatus shown in FIG. 2 corresponds to the apparatus shown in FIG. 1, with the exception that the arrow 18 indicates the direction of the port switching, i.e. the Moving Port principle.

Figure 3:
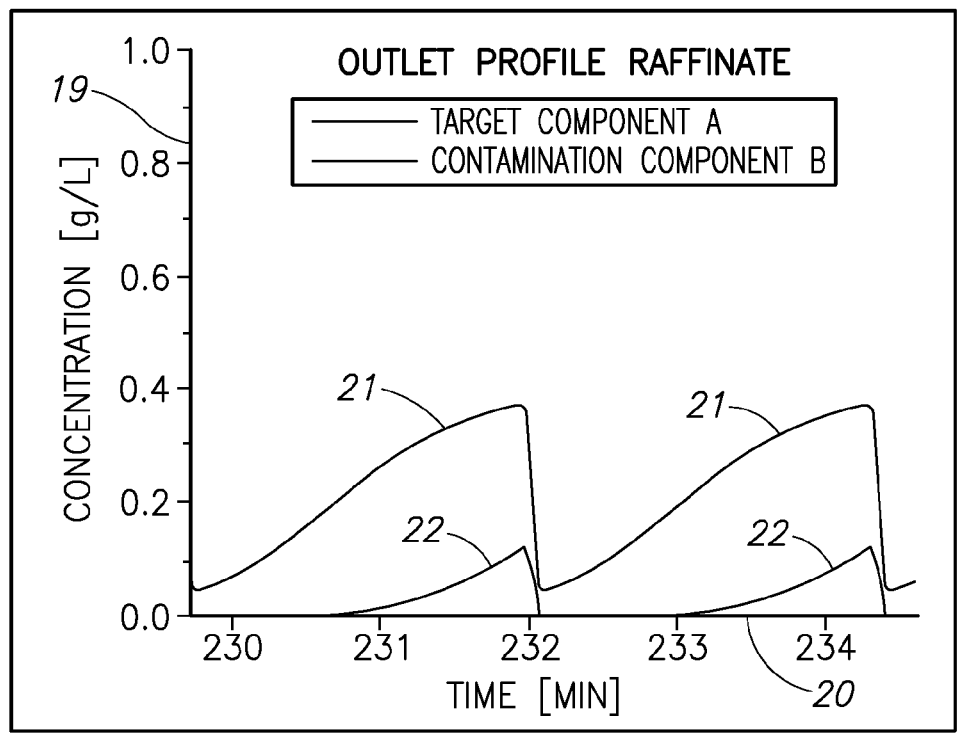
FIG. 3 shows a diagram of exemplary concentration profiles at a raffinate outlet of an apparatus operating with the conventional SMB method.

FIG. 3 shows a diagram of the concentration profile at the raffinate outflow in the apparatus operating with the conventional SMB method. The ordinate 19 shows the concentration of the raffinate stream, i.e. a target component A according to reference numeral 21, and the proportionate contamination component B is identified by the reference numeral 22. The abscissa 20 shows the time course of the concentration.

The time course corresponds to two complete clock units or two complete clock periods. The components to be separated may be present in the multicomponent fluid mix in a high concentration or undissolved and may be diluted or dissolved to a certain concentration prior to the application of the SMB method. For example, both components are present at the same concentration. The conditions applied here are summarised in Table 1 following below and the performance parameters used herein are summarised in Table 2 following below.

Figure 4:
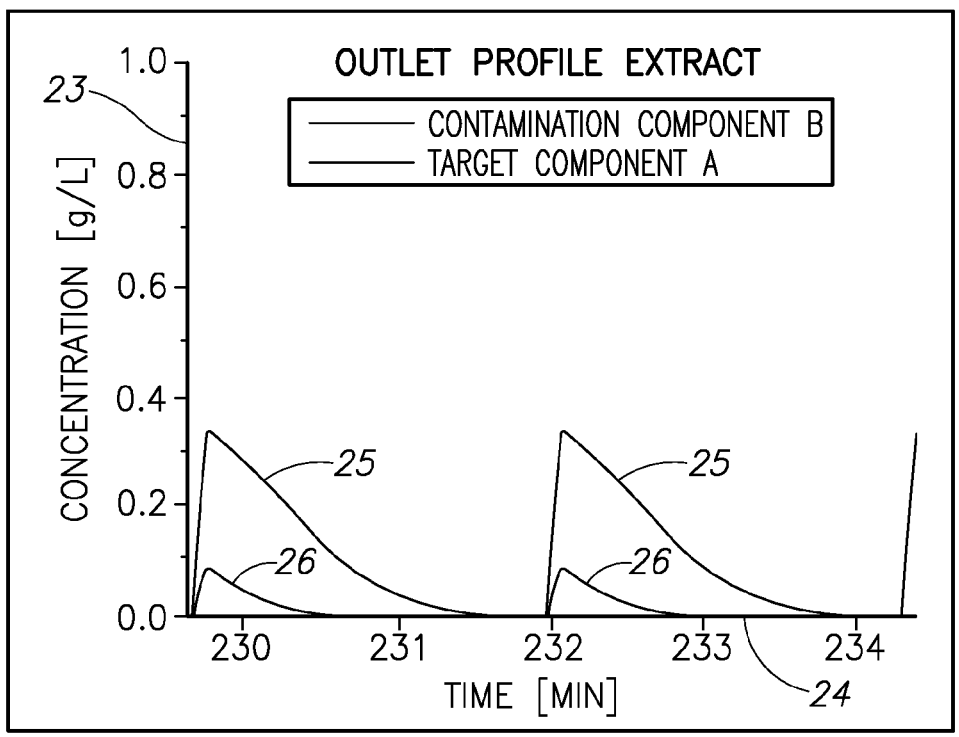
FIG. 4 shows a diagram of exemplary concentration profiles at an extract outlet in an apparatus operating with the conventional SMB method.

FIG. 4 shows a diagram which also illustrates the concentration 23 over the time course 24, the profile of the extract outflow is indicated, which means the time course 25 of the concentration of the target component and the time course 26 of the concentration of the proportionate contamination component A.

By means of the switching processes, a cyclic steady state is achieved with the SMB method. In this state, cyclically constantly repeating concentration profiles may be seen at both outflows. Typically, during a successful operation, the undesired component will not appear until towards the end, such as the component B in the raffinate stream, or only at the beginning, such as the component A in the extract stream, of a clock period.

The emerging streams are collected over the entire period of time. A purity of for example 88% by weight is meant to be achieved integrally averaged across the duration of the entire clock cycle at both outflows.

A clock period may now be subdivided into short subsections of any desired length. At each of the points in time, the differential integral purity achieved at that point in time may be determined at the two outflows. The differential purity indicates the ratio between the concentration of the target component and at least one non-target component emerging from the observed outflow at the current point in time. The integral purity may indicate the ratio between the target component and at least one non-target component emerging from the observed outflow, starting from the beginning of the clock up to the current point in time.

Figure 5:
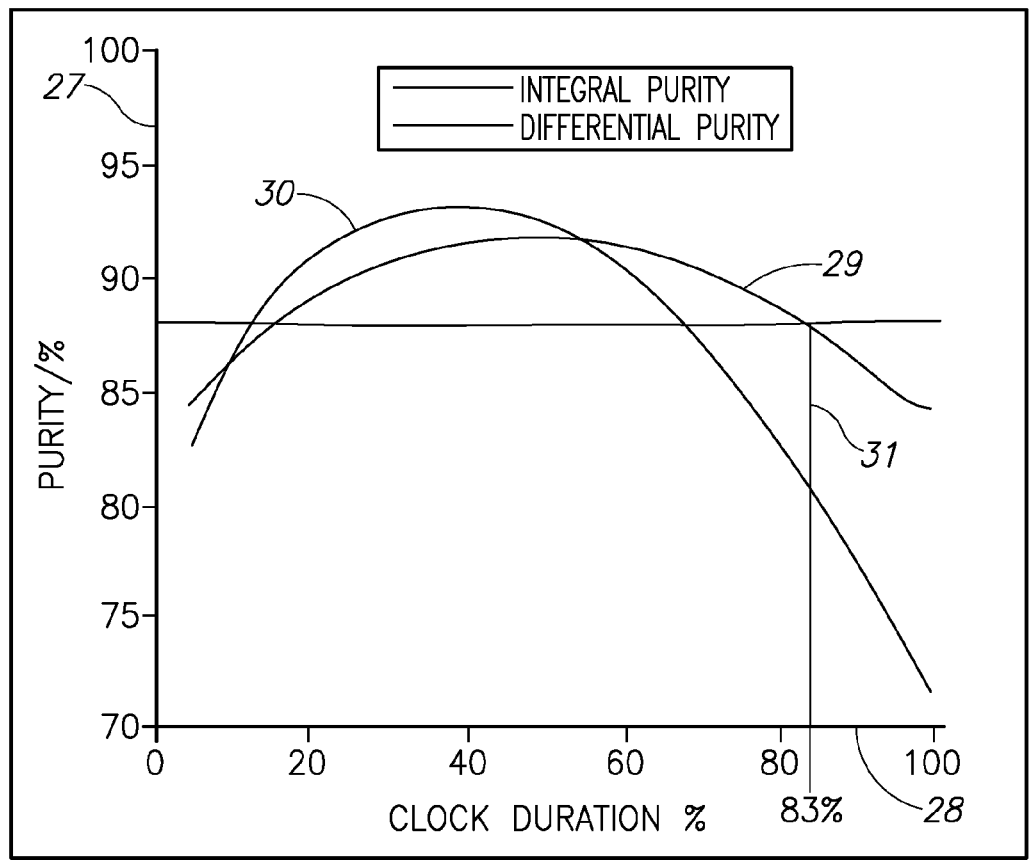
FIG. 5 shows a diagram illustrating an example for the course of an integral and differential degree of purity of the target component in the raffinate stream within a clock period or clock unit in a conventional SMB method.

FIG. 5 shows a diagram of the degree of purity in % along the ordinate 27 and the clock duration in % along the abscissa 28 of the integral purity 29 and the differential purity 30 for the raffinate stream. It is obvious that the integral purity falls below the threshold value of the desired target purity at 83.0% of the clock duration (31).

Figure 6:
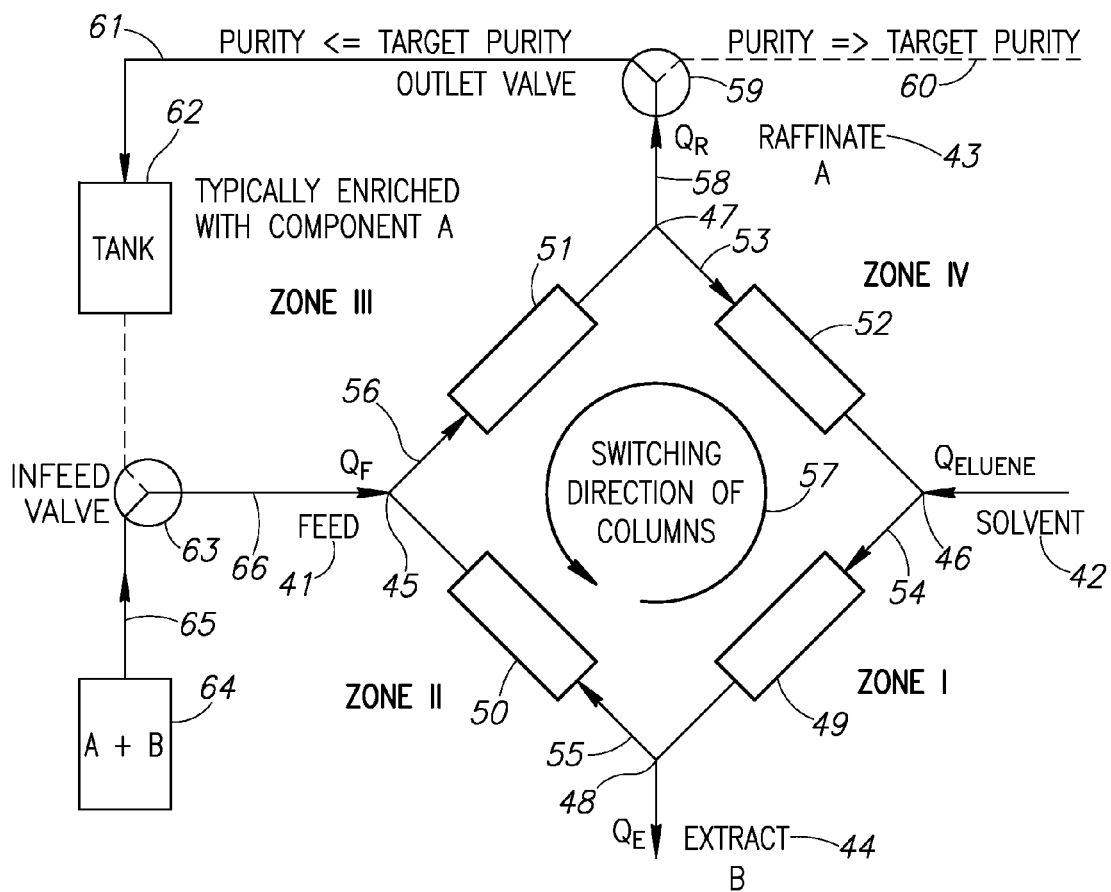
FIG. 6 shows a schematic view of an embodiment of the apparatus for carrying out the method according to the invention.

FIG. 6 shows a schematic view of an embodiment of an apparatus for carrying out the method according to the invention. Here again, a multicomponent fluid mix 41 is fed into the apparatus at an inflow 45 and a solvent 42 at an inflow 46 of the apparatus. Also, a raffinate stream 43 is carried off at an outflow 47 and an extract stream 44 at an outflow 48.

The apparatus in turn consists of a total of four chambers 49, 50, 51 and 52, which are connected to each other in series to form a closed loop. The reference numeral 57 indicates the direction of the column switching.

The arrows 53, 54, 55 and 56 indicate the flow pattern within the chambers and the loop formed thereby.

According to this embodiment of the invention, the outfeed 58 of the raffinate stream 43 at the outlet 47 is guided to an outlet valve 59 wherein a switch-over is carried out as a function of whether a raffinate stream of the required purity of the separated components or of a not required purity is present. If the desired purity is present, a switch-over is carried out in order to drain off the separated component as indicated by the reference numeral 60. If the required purity is not present, a switch-over in the direction 61 is carried out, so that this separated proportion of the raffinate stream is carried into a tank or container 62, which now typically contains a liquid enriched with a component A. Once the end of the clock period is reached, a switch-back to condition 60 is carried out.

A further valve 63, which is formed as an inflow valve, is now switched over as a function of whether the separated raffinate stream stored in the tank 62 is to be circulated back into the chambers via the inflow 45 or whether the initial multicomponent fluid mix 41 is to be fed to a storage tank 64 through an infeed line 65. This is carried out via an infeed line 66.

By means of an apparatus of this kind, it is possible to advantageously apply a combination of collecting a raffinate stream only during a section of the clock period and introducing the collected and preliminarily stored proportion again at a later point in time within one clock unit instead of the original multicomponent fluid mix. If, for example, the 17% of the clock unit, which as shown in FIG. 5 do not meet the purity requirements, are fed back into the chambers by way of such a recirculation of the raffinate stream, the separation result may be improved. This can be seen from Tables 1 and 2 which follow below.

TABLE 1

|  | Conventional Layout[1] | Fractionation Method[2] | Method According to the Invention |
|---|---|---|---|
| Number of Columns |  | 4 |  |
| Column Layout |  | 1/1/1/1 |  |
| Column Dimensions |  | I = 10; d = 1; |  |
| Total Porosity of the Columns $\epsilon$ |  | 0.667 |  |
| Bottom Number N per Column |  | 40 |  |
| $K^A$, $K^B$ |  | 5.078, 5.718 |  |
| Volume Flow in Zone I |  | 9.999 mL/min |  |
| Concentration in the Initial Feed [g/L] |  | 1 each |  |
| Minimum Unit in Both Outlets |  | 88%/88% |  |
| Tank Volume [mL] | — | — | 0.171 |
| Feed Stream $Q_F$ [mL/min] | 0.225 | 0.698 | 0.494 |
| Clock Time $T_S$ [min] | 2.33 | 2.25 | 2.12 |
| Extract Stream $Q_E$ [mL/min] | 1.80 | 1.51 | 1.11 |
| Raffinate Stream $Q_R$ [mL/min] | 0.79 | 1.51 | 1.11 |
| Solvent Stream $Q_{Eluent}$ [mL/min] | 2.36 | 2.33 | 1.73 |
| Feed Concentration $c^F$ [g/L] | 1/1 = constant | 1/1 = constant | 0.68/0.4 (From Recycle Tank) |1/1 |
| Volume Entry from Receiver Tank per Minute [mg/min] | 0.225 | 0.698 | 0.427 |
| Inflow Period from Recycle Tank $T_{inflow}$ [min] | — | — | 0.29 |
| Collection Period in Product Tank $T_{cut}$ [min] |  | 1.81 | 2.02 |
| Recycle Period in Recycle Tank $T_{recycle}$ [min] |  | — | 0.1 |
| m Streams [—] | 6.9/5.3/5.5/4.8 | 6.6/5.3/5.9/4.6 | 6.1/5.2/5.6/4.7 |
| Intersections [—] | — | 17 [of 23] | 21 [of 22] |
| Inflow Points [—] | — | — | 3 [of 22] |
| Volume Difference per Clock [mL] | — | — | −0.0357 |

[1]according to U.S. Pat. No. 2,985,589
[2]according to Journal of Chromatography A 1122 (2006) 161

Table 1 shows selected simulation parameters for the target function, the product of raffinate purity and productivity multiplied by extract purity and productivity.

The dimensionless intersections and infeed points are a result of the discretisation of a clock period into 23 (fractionation method) or 22 (method according to the invention) points. The volume difference indicates that under the selected conditions, 0.0357 ml more per switch-over time would be pumped out of the tank than can be fed into it by recirculation. This difference is compensated for by means of a suitable stream of pure solvent.

TABLE 2

|  | Conventional Layout[1] | Fractionation Method[2] | Method According to the Invention | Increase/Reduction Compared to Other Methods [%] | |
|---|---|---|---|---|---|
|  |  |  |  | Conventional | Fractionation |
| Purity Raffinate [%] | 88.2 | 88.8 | 88.0 | — |  |
| Purity Extract [%] | 88.1 | 88.1 | 89.0 | — |  |
| $C_{Extract}$ [g/L] | 0.106 | 0.305 | 0.326 | 208 | 7 |
| $C_{Raffinate}$ [g/L] | 0.220 | 0.279 | 0.319 | 45 | 14 |
| Product Volume Stream A [mg/min] | 0.173 | 0.311 | 0.338 | 96 | 9 |
| Product Volume Stream B [mg/min] | 0.19 | 0.460 | 0.363 | 90 | −21 |
| Productivity A [mg/mL * min] | 0.0166 | 0.030 | 0.032 | 95 | 9 |
| Productivity B [mg/mL * min] | 0.0182 | 0.044 | 0.035 | 90 | −21 |
| Eluant Consumption EC A [mL/mg] | 14.91 | 9.71 | 6.57 | −56 | −32 |
| Eluant Consumption EC B [mL/mg] | 13.55 | 6.57 | 6.13 | −55 | −7 |
| Yield A [%] | 77.2 | 44.6 | 79.3 | 3 | 78 |
| Yield B [%] | 85.0 | 66.0 | 85.0 | 0 | 29 |
| Loss A [%] | 11.5 | 45.9 | 10.5 | −9 | −77 |
| Loss B [%] | 10.4 | 22.1 | 10.8 | 4 | −51 |

[1] according to U.S. Pat. No. 2,985,589
[2] according to Journal of Chromatography A 1122 (2006) 161

In Table 2, important performance parameters are compared with each other.

The percentage changes are calculated as follows:

$$\text{Change } [\%] = \frac{100}{Value_{conventional/fractionation}} Value_{invention} - 100$$

It is to be noted that for the consumption and loss of eluant, a lower value is better. The definitions are briefly given below.

The product volume flow from the raffinate for the fractionation method as well as the method according to the invention:

$$\dot{m}_i^{Ra} = \frac{Q_R * \int_{(x-1)*T_S}^{(x-1)*T_S + T_{cut}} c_i(t) dt}{T_S}$$

For the conventional SMB method, the following applies:

$$\dot{m}_i^{Ra} = \frac{Q_R * \int_{(x-1)*T_S}^{x*T_S} c_i(t) dt}{T_S}$$

In all cases, the product volume flow in the extract is calculated as follows:

$$\dot{m}_i^{Ex} = \frac{Q_E * \int_{(x-1)*T_S}^{x*T_S} c_i(t) dt}{T_S}$$

The purity of the raffinate is:

$$Pur^{Ra} = 100 * \frac{\dot{m}_A^{Ra}}{\sum_{\gamma=1}^{NC} \dot{m}_\gamma^{Ra}}$$

The purity of the extract is:

$$Pur^{Ex} = 100 * \frac{\dot{m}_B^{Ex}}{\sum_{\gamma=1}^{NC} \dot{m}_\gamma^{Ex}}$$

The productivity for component A is:

$$PR_A = \frac{\dot{m}_A^{Ra}}{\text{Number of Columns} * (1 - \varepsilon) * \text{Column Volume}}$$

The productivity for component B is:

$$PR_B = \frac{\dot{m}_B^{Ex}}{\text{Number of Columns} * (1 - \varepsilon) * \text{Column Volume}}$$

For the solvent consumption (EC) the following applies:

$$EC_A = \frac{Q_{Eluant} + Q_F}{\dot{m}_A^{Ra}} \text{ or } EC_B = \frac{Q_{Eluant} + Q_F}{\dot{m}_B^{Ex}}$$

For the yield in the fractionation method and the method according to the invention the following applies:

$$Yield_A = \frac{in_A^{Ra}}{Q_F * c_A^F * T_{inflow}/T_S}$$

$$Yield_B = \frac{in_B^{Ex}}{Q_F * c_B^F * T_{inflow}/T_S}$$

For the yield for the conventional SMB method the following applies:

$$Yield_A = \frac{\dot{m}_A^{Ra}}{Q_F * c_A^F}$$

$$Yield_B = \frac{\dot{m}_B^{Ex}}{Q_F * c_B^F}$$

For the loss in the conventional method and the method according to the invention the following applies:

$$Loss_A = \frac{in_A^{Ex}}{Q_F * c_A^F * T_{inflow}/T_S}$$

$$Loss_A = \frac{in_{RA}^{Ra}}{Q_F * c_B^F * T_{inflow}/T_S}$$

For the fractionation method the following applies:

$$Loss_A = \frac{\dot{m}_A^{Ex} + Q_R * \int_{(j-1)*T_S+T_{cut}}^{j*T_S} c_A(t)\,dt}{Q_F * c_A^F * T_S}$$

$$Loss_B = \frac{\dot{m}_B^{Ra} + Q_R * \int_{(j-1)*T_S+T_{cut}}^{j*T_S} c_B(t)\,dt}{Q_F * c_B^F * T_S}$$

For the case of a target purity of at least 80%, which is selected as an example, a wide range of parameters was used in simulation studies, and a working point was selected therefrom as an example, which has the highest value for the target function, the quotient from the product of purity and productivity of raffinate and extract. The parameters resulting therefrom are summarised in Table 1, the performance parameters in Table 2.

For a simulation of the system, the extended equilibrium model known from literature (G. Golshan-Shirazi and A. M. Katti, Fundamentals of Preparative and Nonlinear Chromatography, Academic Press, Boston, Mass. (1994)) was used. The numerical calculation is carried out by means of the Rouchon algorithm (P. Rouchon, M. Schonauer, P. Valentin and G. Guiochon, Sel. Sci. Technol. 22 (1987, p. 1793)). The concentrations in the solid and liquid phases are linked via the adsorption isotherms. In the observed case, this is a linear isotherm.

In Table 1 of 2, the process parameters and performance parameters for three different methods are shown, namely one according to the U.S. Pat. No. 2,985,589 as a conventional SMB method, a fractionation method (Y.-S. Bae and C.-H. Lee, "Partial discard strategy for obtaining high purity products using simulated movid bed chromatography") and a method according to the invention. Each of these methods was selected based on the requirement that at a given minimum purity of 88%, if possible, maximum values for the product of raffinate purity and productivity obtained from a component A as well as the product of extract purity and productivity obtained from a component B are to be achieved. The adsorption behaviour of both components may be described by means of linear isotherms.

The method according to the invention may be realised in different ways. For the case of a recirculation of raffinate, the product collection period within the clock unit or the clock period is limited by the start of a clock unit and the point in time at which the integral purity falls below the required threshold value. From this, a differential time period between the end of the product collection period and the beginning of the next clock unit results. The stream emerging within this period of time no longer meets the purity requirements and will be collected in at least one tank, the content of which is also fed to the inflow 45 in periodic intervals.

In the case of a recirculation of extract, the integral purity increases with increasing clock duration and contamination will set in at the beginning of a clock period. The integral purity is determined starting at the end of the clock unit and going backwards in the direction of the start of the clock period. Thus, the product collection period is limited by the beginning of the collection and the end of the clock unit.

In the case of both raffinate and extract recirculation as well as in the case of a combination of both, the rate of efficiency of this method and of the apparatus for carrying out this method is influenced by the duration and the point in time of the recirculation.

For example, the effluent stream will be collected only up to a point in time before the value falls below the threshold. According to FIGS. 3 and 4, this corresponds to 83%. This proportion will be collected in a product tank at the end of line 60 (not shown). For the remaining 17% of the clock unit, the raffinate stream is collected in the tank 62. From there, it will be fed to the inflow 45 alternately with the initial multicomponent fluid mix. This recirculation of a raffinate stream, the concentration ratio of which is typically already shifted in favour of one of the components, will then again lead to an increase in the purity of the output raffinate stream 43 concerned by the recirculation.

The duration of the recirculation is determined predominantly by the selection of the product collection period. The recirculation period typically lies between the beginning of the clock unit and the end of the clock unit. For the case of the raffinate recirculation it is advantageous to realise the backflow from the tank 62 at the beginning of the clock unit. For the case of the recirculation of extract, this should be exactly the other way around, i.e. at the end of the clock unit.

As soon as the point in time is reached at which the purity falls below the target purity value, the outlet valve 59 is switched in such a way that the raffinate stream is diverted into the tank 62 for the remainder of the clock period. The inflow valve will then control when the inflow into the chambers via the inflow 45 from the tank 62 or, instead, the inflow of the initial multicomponent fluid mix from the container 64, is to be carried out. According to this embodiment, the extract stream will be continuously collected and carried off.

Figure 7:
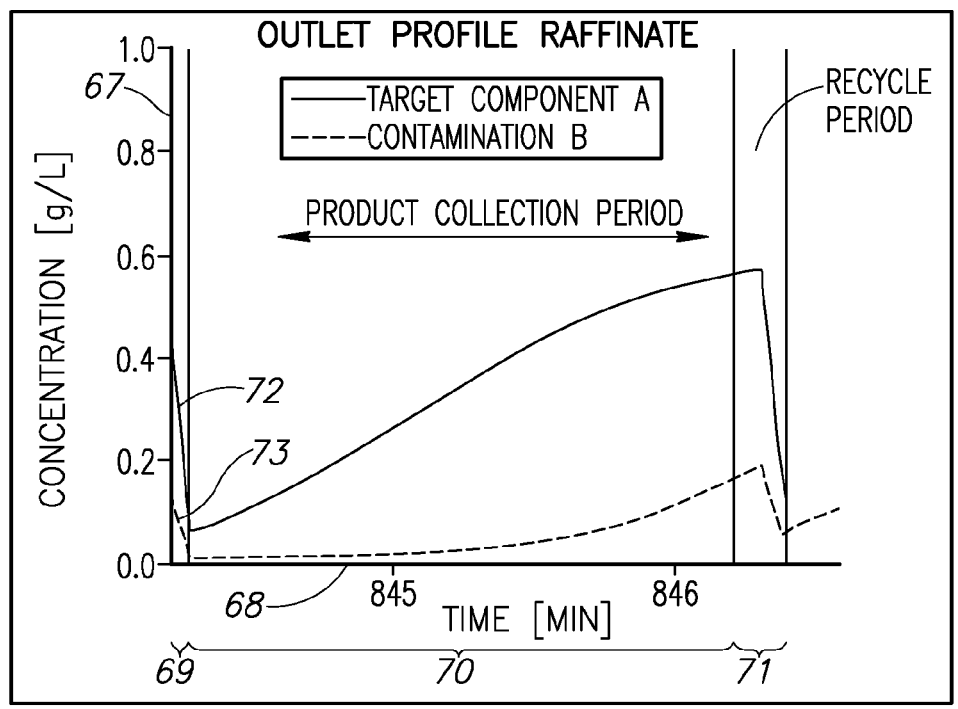
FIG. 7 shows a diagram of exemplary concentration profiles of the raffinate stream of an apparatus operating with the SMB method according to the invention.
Figure 8:
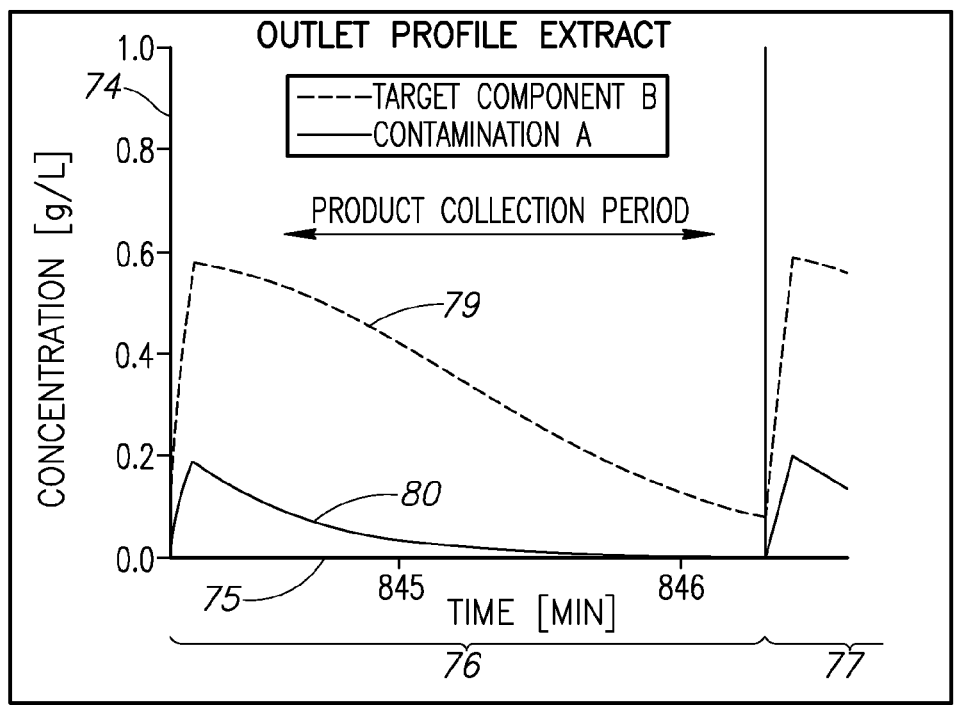
FIG. 8 shows a diagram of exemplary concentration profiles of the extract stream of an apparatus operating with the SMB method according to the invention.

FIG. 7 and FIG. 8 show diagrams of the time courses of the concentration profiles of the raffinate stream and of the extract stream along the ordinates 67 and 74, respectively, and the abscissas 68 and 75, respectively. The concentration profiles are identified for the target component A by means of the reference numeral 72, for the target component B in the case of the extract stream by means of the reference numeral 79, for the proportionate contamination component B by means of the reference numeral 73 and for the proportionate contamination component A by means of the reference numeral 80.

A working point was selected from a data field determined by simulation for a minimum purity of 88% selected as an example. The observed conditions are again summarised in Table 1, the determined performance parameters in Table 2.

It can be seen from the tables that the average outflow concentration of component A in the raffinate stream was increased by 45% compared to the conventional method and by 14% compared to the fractionation method without recirculation. The average outflow concentration of component B in the extract stream may be increased by 208% compared to the conventional method. Compared to the fractionation method, it is increased by 7%.

The volume stream of component A from the raffinate stream that can be achieved may be increased by 96% compared to the conventional method and by 9% compared to the fractionation method. The volume stream of component B from the extract stream that can be achieved may be increased by 90% compared to the conventional method, but is reduced by 39% compared to the fractionation method. However, this is achieved at the cost of a markedly lower yield and a high component loss.

The productivity for component A from the raffinate stream may be increased by 95% compared to the conventional method and by 9% compared to the fractionation method. The productivity for component B from the extract stream may be increased by 90% compared to the conventional method.

The specific solvent consumption for component A from the raffinate stream may be reduced by 56% compared to the conventional method and by 32% compared to the fractionation method. The specific solvent consumption for component B from the extract stream may be reduced by 55% compared to the conventional method and by 7% compared to the fractionation method.

The yield for component A from the raffinate stream may be increased by 3% compared to the conventional method and by 78% compared to the fractionation method. The yield for component B from the extract stream remains at the same level as in the conventional method and is increased by 29% compared to the fractionation method.

The loss of component A is by 9% below the level of the conventional method, it may be reduced by 77% compared to the fractionation method. The loss of component B is increased by 4% compared to the conventional method, but is reduced by 51% compared to the fractionation method.

Sections 70 and 71 indicate the product collection period, which means the period in which the product is carried off from the entire apparatus at the desired purity, and the recycle period, which means the period in which the raffinate stream is separated off to a recirculation point. Section 69 partially indicates a preceding cycle. In addition, a subsequent cycle is partially indicated.

Sections 76, 77 of FIG. 8 show almost 2 cycles of the extract stream.

The enhancement of the efficiency compared to the conventional method is achieved by virtue of the fact that the targeted final purity of the streams no longer has to be integrally present over the entire clock time, but only up to an earlier point in time. For this reason, higher feed streams and lower regeneration streams are possible. This allows an increase of productivity. Due to the reduction in eluant consumption as well as the possibility to achieve a high separation efficiency even with less efficient and thus cheaper solid materials, the operating costs may be reduced.

The fractionation method described in literature also has the advantage that the desired target purity does not need to be integrally present over the entire switching time. However, the method according to the invention characterises itself from the fractionation method in an advantageous manner in the following points.

Since the volume proportion collected as the product is not discarded but is reintroduced, the yield may be increased and the component loss may be markedly reduced. The recirculation itself has a positive effect on the purities that may be achieved and thus also on the productivity. If, as in the exemplary case shown in Table 2, the strength of the interaction of the components with the solid phase is independent from the concentration and other components involved, linear adsorption isotherms are present. For the case of the recirculation of raffinate it is advantageous to introduce the pre-separated mix prior to the initial multicomponent fluid mix. In this way, a lower amount of components which are undesired at this outflow is introduced at the beginning of the clock unit. By means of a renewed passage of the separating solid phase, the purity is increased even further. Since the mix introduced into the system at the beginning of the clock unit is also the first to reach the outflow, and in the observed case of the recirculation of raffinate, the proportion to be collected is also at the beginning, the purity to be achieved may be increased compared to the fractionation method under the same conditions with regard to the working points of the separation as well as the collection period in the product tank.

The opposite applies to the case of recirculation extract. Here, a later introduction of the content of the recycle tank is advantageous.

If the strength of the interaction of the components with the solid phase is a function of its inherent concentration as well as that of the other components involved, i.e. if non-linear adsorption isotherms are present, any improvement of the purities is conditioned by competitive interactions.

Of course, any type of different preliminary stores may be used instead of a container serving as a preliminary store, such as for example chromatography columns.

The recirculation stream may also be introduced directly without any intermediate storage.

The method according to the invention may be applied to any conceivable SMB constructions so far known, which may for example have more or less than four chambers. For example, such a construction may consist of 1-3 or 5 or more chambers.

All of the features disclosed in the application materials are claimed as essential to the invention in so far as they are novel compared to the prior art either individually or in combination.

The embodiments of the invention in which an exclusive property or privilege is claimed are defined as follows:

1. A method for the chromatographic separation of components of a multicomponent fluid mix using the Simulated Moving Bed method, comprising:
   inputting the multicomponent fluid mix and at least one solvent to a plurality of chambers or chamber sections containing at least one solid substance via at least one of first and second inflows of having connection ports disposed between the chambers or chamber sections, wherein the chambers or chamber sections are connected to each other in series to substantially form a loop;
   outputting from the chambers or chamber sections through at least one of first and second outflows having connection ports disposed between the chambers or chamber sections an extract stream containing at least one first component separated from the multicomponent fluid mix and a raffinate stream containing at least one second component separated from the component fluid mix;

wherein the connection ports of the first and second inflows and outflows are newly positioned between two further chambers or chamber sections of the loop within a cyclic clock unit;

storing at least part of at least one of the extract stream or the raffinate stream output from the chambers or chamber sections through at least one of the first and second outflows; and recirculating to at least one of the first and second inflows of the chambers or chamber sections at least one of the extract stream or the raffinate stream within a clock unit either alternately or simultaneously with inputting at least one of the multicomponent fluid mix or the solvent to the at least one of the first and second inflows.

2. The method of claim 1, wherein recirculating at least one of the extract stream or the raffinate stream output from the chambers or chamber sections occurs within a clock unit following outputting.

3. The method of claim 1, wherein recirculating at least one of the extract stream or the raffinate stream output from the chambers or chamber sections occurs within the same clock unit at outputting.

4. The method of claim 1, wherein:
a clock unit has a plurality of segments;
at least one of the entire raffinate stream or extract stream output from the chambers or chamber sections has a predetermined degree of purity; and
at least one of the entire raffinate stream or extract stream output from the chambers or chamber sections is recirculated within at least one segment of the clock unit.

5. The method of claim 1, wherein a pressure of the input multicomponent fluid mix or the solvent is modified within a clock unit in one of a stepwise or continuous mode.

6. The method of claim 1, wherein a temperature of the input multicomponent fluid mix or the solvent is modified within a clock unit in one of a stepwise or continuous mode.

7. The method of claim 1, wherein the composition of at least one of the multicomponent fluid mix or the solvent is modified in a stepwise or continuous mode.

8. The method of claim 1, wherein the at least one solid substance within the individual chambers or chamber sections is suitable for causing different velocities of movement of at least one of the individual components comprising the multicomponent fluid mix.

9. The method of claim 8, wherein the solid substance is an adsorbent material.

10. The method of claim 1, wherein the solvent consists of at least one of a mixture of a plurality of fluids or a mixture of at least one fluid with at least one low or high molecular modifier.

11. The method of claim 1, wherein the solvent consists of at least one of a gas or a mixture of a plurality of gases in the supercritical or the sub-critical condition.

12. The method of claim 1, wherein the solvent contains components to be separated.

13. The method of claim 12, wherein:
at least two solvents are input, a first solvent containing components to be separated and a second solvent without components to be separated; and
the first and second solvents have different characteristics with regard to influencing a binding behaviour of the components to be separated compared to the solid substance.

14. The method of claim 1, wherein a chemical reaction for producing and separating the components is carried out in the chambers or chamber sections.

15. The method of claim 1, wherein the connection ports of the first and the second inflows and outflows are newly positioned at different points in time.

16. The method of claim 1, wherein at least one of the multicomponent fluid mix, the solvent, the extract stream the raffinate stream, and a recirculating stream is modified within a clock unit in a stepwise or continuous mode.

17. The method of claim 1, wherein the loop is an open loop.

18. The method of claim 1, wherein the multicomponent fluid mix consists of at least one of a gas or a mixture of a plurality of gases in the supercritical or the sub-critical condition.

19. The method of claim 1, wherein the loop is a closed loop.

20. The method of claim 1, wherein the at least part of at least one of the extract stream or the raffinate stream output from the chambers or chamber sections through at least one of the first and second outflows is preliminary stored in a container.

* * * * *